United States Patent [19]

Umezawa et al.

[11] 4,360,664
[45] Nov. 23, 1982

[54] ANTHRACYCLINE GLYCOSIDE 14-HALO,4'-ETHER

[75] Inventors: Hamao Umezawa; Tomio Takeuchi; Hiroshi Naganawa; Kuniaki Tatsuta, all of Tokyo, Japan

[73] Assignee: Zaidan Hojin Biseibutsu Kagaku Kenkyu Kai, Tokyo, Japan

[21] Appl. No.: 253,489

[22] Filed: Apr. 13, 1981

[30] Foreign Application Priority Data

Apr. 26, 1980 [JP] Japan ................................. 55-55974

[51] Int. Cl.³ ............................................ C07H 15/24
[52] U.S. Cl. ..................................................... 536/6.4
[58] Field of Search ....................................... 536/17 A

[56] References Cited

U.S. PATENT DOCUMENTS

| | | | |
|---|---|---|---|
| 3,590,028 | 6/1971 | Arcamone et al. | 536/17 A |
| 3,616,242 | 10/1971 | Belloc | 536/17 A |
| 3,803,124 | 4/1974 | Arcamone et al. | 536/17 A |
| 4,169,142 | 9/1979 | Penco et al. | 536/17 A |
| 4,225,589 | 9/1980 | Ducep et al. | 536/17 A |

FOREIGN PATENT DOCUMENTS

| | | | |
|---|---|---|---|
| 14853 | 9/1980 | European Pat. Off. | 536/17 A |
| 2002754 | 2/1979 | United Kingdom | 536/17 A |

*Primary Examiner*—Johnnie R. Brown
*Attorney, Agent, or Firm*—David M. Morse

[57] ABSTRACT

A new and improved process for the preparation of C-4' etherified anthracycline glycoside derivatives is provided. The new process involves fewer steps than the prior art process and gives the antibiotic end-products in higher yield.

3 Claims, No Drawings

ANTHRACYCLINE GLYCOSIDE 14-HALO,4'-ETHER

BACKGROUND OF THE INVENTION

1. Field of the Invention

This invention relates to a new and improved process for the preparation of certain known anthracycline glycoside antibiotics. Also provided are novel intermediates useful in the above process.

2. Description of the Prior Art

Both the starting materials, daunomycin and its acid addition salts, and active end-products, C-4' etherified derivatives of adriamycin, prepared according to the present invention are known. Daunomycin (and its acid addition salts) is disclosed, for example, in U.S. Pat. No. 3,616,242. Adriamycin is disclosed in U.S. Pat. No. 3,590,028. The C-4' etherified derivatives of adriamycin produced by the process of the present invention are disclosed in U.K. patent application No. 2,002,754A and European patent application No. 14,853.

The halogenation of a daunomycin starting material to produce 14-halodaunomycin intermediates is disclosed in U.S. Pat. No. 3,803,124 as is the alkaline hydrolysis of these intermediates to give adriamycin. No suggestion of using the 14-halodaunomycin intermediate to produce C-4' etherified adriamycin derivatives is made in this reference.

U.S. Pat. No. 4,225,589 discloses bromination of daunomycin to give a 14-bromodaunomycin dimethylketal intermediate and the conversion of this ketal to a 14-bromodaunomycin by deketalisation with a ketone in the presence of hydrochloric acid. No disclosure is given, however, of the use of either of these intermediates to produce C-4' etherified adriamycin derivatives.

SUMMARY OF THE INVENTION

This invention relates to a new and improved process for preparation of C-4' etherified anthracycline glycoside derivatives having the general formula

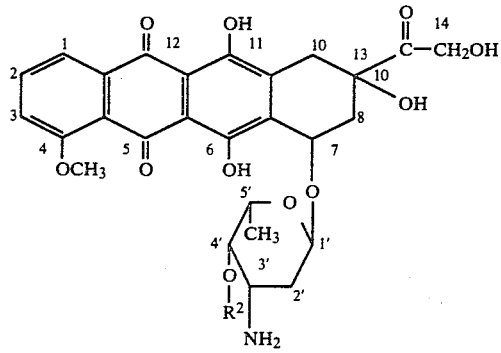

wherein $R^2$ is tetrahydropyranyl, 6-acetoxymethyltetrahydropyranyl, 6-methoxytetrahydropyranyl, 6-carbomethoxytetrahydropyranyl, tetrahydrofuranyl, $C_1$–$C_8$ alkyloxyethyl or cyclohexyloxyethyl, or acid addition salts thereof. The compounds of formula I and their nontoxic acid addition salts exhibit both antimicrobial and antitumor activity.

In its most complete aspect, the present invention provides a process for preparation of compounds of formula I and acid addition salts thereof, which process comprises the steps of (1) halogenating daunomycin or an acid addition salt thereof in an inert organic solvent to produce a mixture of a 14-halodaunomycin dimethylketal intermediate of the formula

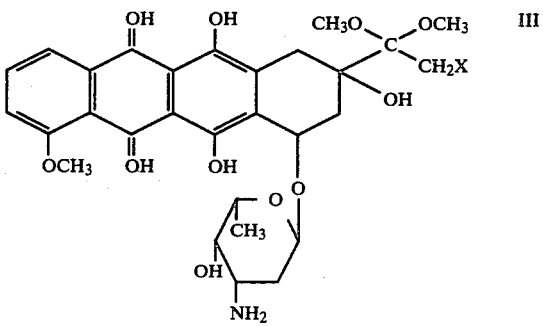

wherein X is a halogen atom, or an acid addition salt thereof, and a 14-halodaunomycin intermediate of the formula

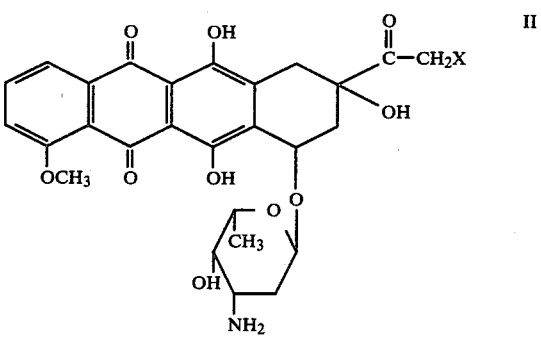

wherein X is a halogen atom, or an acid addition salt thereof;

(2) treating the mixture of intermediates from step (1) with acetone for a sufficient time to effect conversion of the dimethylketal intermediate III to the ketone intermediate II;

(3) reacting the 14-halodaunomycin intermediate II or acid addition salt thereof with dihydrofuran, dihydropyran, 2-acetoxymethyl-3,4-dihydro-2H-pyran, 2-methoxy-3,4-dihydro-2H-pyran, 2-carbomethoxy-3,4-dihydro-2H-pyran or an alkyl vinyl ether of the formula $CH_2=CHOR^1$ in which $R^1$ is $C_1$–$C_8$ alkyl or cyclohexyl in an inert organic solvent and in the presence of an acid catalyst to produce a C-4' etherified intermediate of the formula

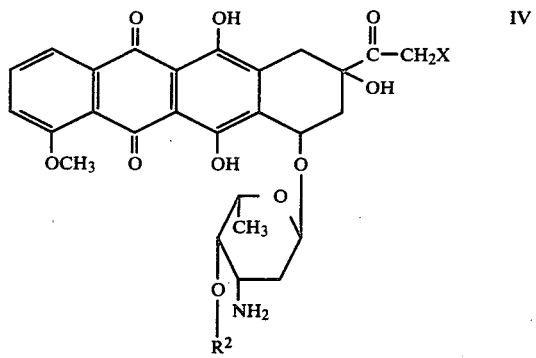

wherein X is as defined above and $R^2$ is tetrahydropyranyl, 6-acetoxymethyltetrahydropyranyl, 6-methoxytetrahydropyranyl, 6-carbomethoxytetrahydropyranyl, tetrahydrofuranyl, $C_1$–$C_8$ alkyloxyethyl or cyclohexyloxyethyl, or an acid addition salt thereof; and (4) subjecting intermediate IV or an acid addition salt thereof to alkaline hydrolysis to produce the desired compound of formula I, or acid addition salt thereof.

In another aspect, the present invention provides the process of preparing the formula I compounds or acid addition salts thereof from 14-halodaunomycin intermediate II, which process comprises the steps of (1) reacting a 14-halodaunomycin intermediate of the formula

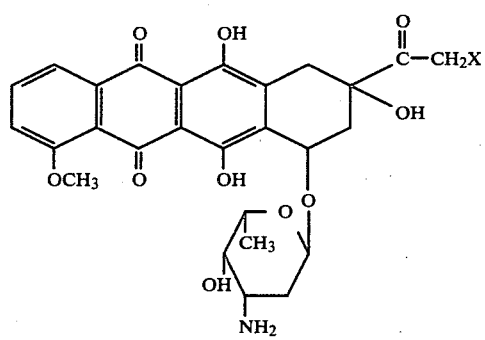

wherein X is a halogen atom, or an acid addition salt thereof, with dihydrofuran, dihydropyran, 2-acetoxymethyl-3,4-dihydro-2H-pyran, 2-methoxy-3,4-dihydro-2H-pyran, 2-carbomethoxy-3,4-dihydro-2H-pyran or an alkyl vinyl ether of the formula $CH_2=CHOR^1$ in which $R^1$ is $C_1$–$C_8$ alkyl or cyclohexyl in an inert organic solvent and in the presence of an acid catalyst to produce a C-4' etherified intermediate of the formula

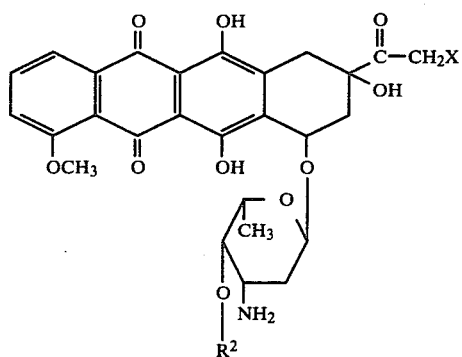

wherein X is as defined above and $R^2$ is tetrahydropyranyl, 6-acetoxymethyltetrahydropyranyl, 6-methoxytetrahydropyranyl, 6-carbomethoxytetrahydropyranyl, tetrahydrofuranyl, $C_1$–$C_8$ alkyloxyethyl, or cyclohexyloxyethyl, or an acid addition salt thereof; and (2) subjecting intermediate IV or an acid addition salt thereof to alkaline hydrolysis.

In still another aspect, the present invention provides the process of preparing the formula I compounds or acid addition salts thereof from the novel C-4' etherified intermediates of formula IV, which process comprises subjecting an intermediate having the formula

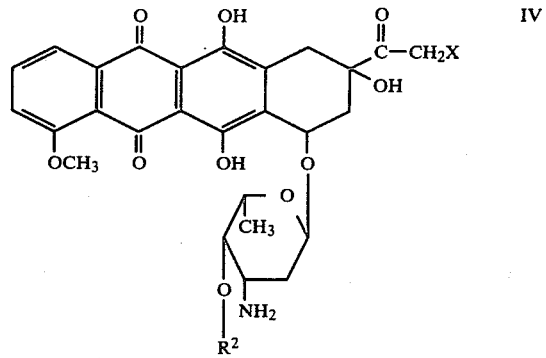

wherein X is a halogen atom and $R^2$ is tetrahydropyranyl, 6-acetoxymethyltetrahydropyranyl, 6-methoxytetrahydropyranyl, 6-carbomethoxytetrahydropyranyl, tetrahydrofuranyl, $C_1$–$C_8$ alkyloxyethyl, or cyclohexyloxyethyl, or an acid addition salt thereof, to alkaline hydrolysis.

In yet another aspect, the present invention provides the novel intermediates of formula IV and acid addition salts thereof together with the process of preparing such intermediates by reacting an intermediate having the formula

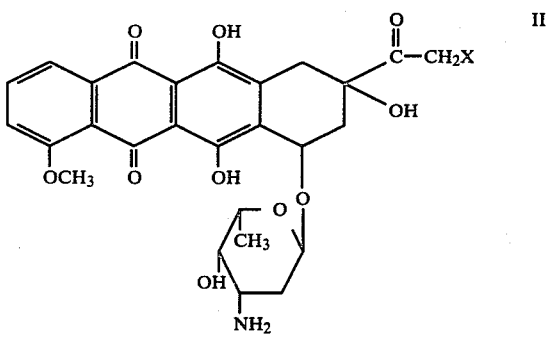

wherein X is a halogen atom, or an acid addition salt thereof, with dihydrofuran, dihydropyran, 2-acetoxymethyl-3,4-dihydro-2H-pyran, 2-methoxy-3,4-dihydro-2H-pyran, 2-carbomethoxy-3,4-dihydro-2H-pyran or an alkyl vinyl ether of the formula $CH_2=CHOR^1$ in which $R^1$ is $C_1$–$C_8$ alkyl or cyclohexyl in an inert organic solvent and in the presence of an acid catalyst.

DETAILED DESCRIPTION

As used herein and in the claims in term "nontoxic acid addition salt" is meant to include salts containing anions which in therapeutic doses of the salts are relatively inocuous to the host organism so that the beneficial antimicrobial and antitumor properties in the bases are not adversely affected by side-effects resulting from the anions. Illustrative examples would be salts formed from such pharmaceutically acceptable acids as sulfuric, phosphoric, hydrochloric, hydrobromic, nitric, phosphorous, acetic, propionic, maleic, oleic, palmitic, citric, succinic, tartaric, fumaric, glutamic, pantothenic, laurylsulfonic, methanesulfonic, naphthalenesulfonic, etc. The term "acid addition salt" as used herein is meant to include nontoxic acid addition salts and also other acid addition salts which may be to some degree be toxic to the host organism but which can be converted by known methods to nontoxic acid addition salts or to the free base compounds. The acic addition salts which are not pharmaceutically acceptable are useful as intermediates in the preparation of the active end-products, i.e. the compounds of formula I and non-toxic acid addition salts thereof.

The C-4' etherified anthracycline glycoside derivatives of formula I above have been found to be useful antimicrobial and antitumor agents.

U.K. patent application No. 2,002,754A discloses inter alia preparation of the tetrahydropyranyl ether derivative of the formula

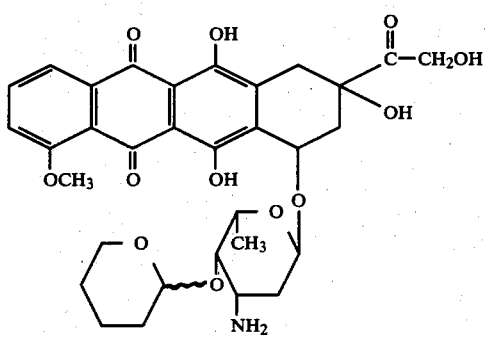

by reacting adriamycin or an acid addition salt thereof with dihydropyran in an inert organic solvent and in the presence of an acid catalyst to convert the C-4' and C-14 hydroxyl groups to tetrahydropyranyloxy groups and then selectively converting the C-14 tetrahydropyranyloxy group to a hydroxyl group by hydrolysis or alcoholysis.

European patent application No. 14,853 discloses inter alia preparation of adriamycin C-4' etherified derivatives of formula I above by a four step process starting with daunomycin, i.e. (1) bromination of daunomycin to obtain the C-14 position brominated daunomycin derivative of the formula

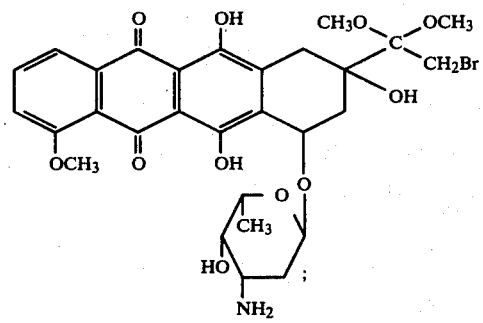

(2) reaction of intermediate IIIa with a compound of formula $R^3COOH$ wherein $R^3$ is $C_1$-$C_6$ alkyl or a benzyl group, or an alkali metal salt thereof, to obtain an ester intermediate of the formula

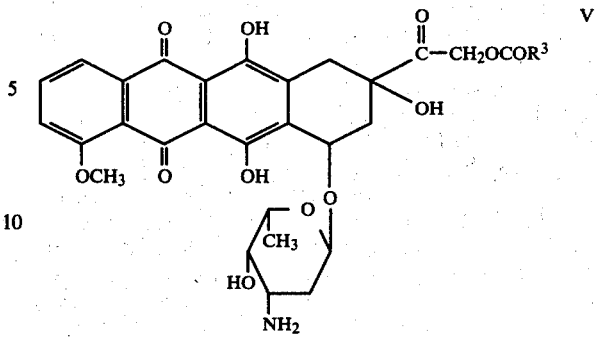

wherein $R^3$ is as defined above; (3) reaction of ester V with dihydrofuran, dihydropyran, 2-acetoxymethyl-3,4-dihydro-2H-pyran, 2-methoxy-3,4-dihydro-2H-pyran, 2-carbomethoxy-3,4-dihydro-2H-pyran or an alkyl vinyl ether of the formula $CH_2=CHOR^1$ in which $R^1$ is $C_1$-$C_8$ alkyl or cyclohexyl in an inert organic solvent and in the presence of an acid catalyst to produce a C-4' position substituted derivative of the formula

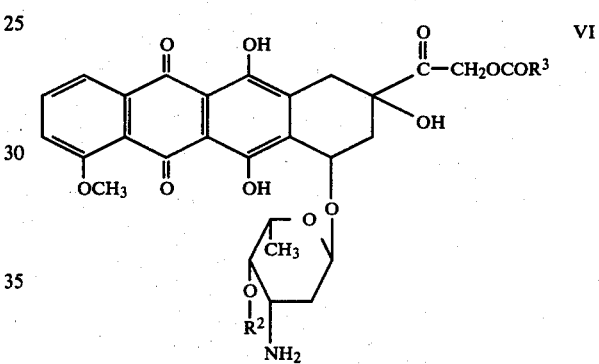

wherein $R^3$ is as defined above and $R^2$ is tetrahydropyranyl, 6-acetoxymethyltetrahydropyranyl, 6-methoxytetrahydropyranyl, 6-carbomethoxytetrahydropyranyl, tetrahydrofuranyl, $C_1$-$C_8$ alkyloxyethyl, or cyclohexyloxyethyl, or an acid addition addition salt thereof; and (4) hydrolytic desacylation of intermediate VI with alkali in a lower alcohol or aqueous acetone solvent system to obtain the desired product I.

It has been found that when daunomycin is brominated according to the process of European patent application No. 14,853, there is obtained a mixture of the 14-bromodaunomycin dimethylketal intermediate IIIa mentioned above and 14-bromodaunomycin having the formula

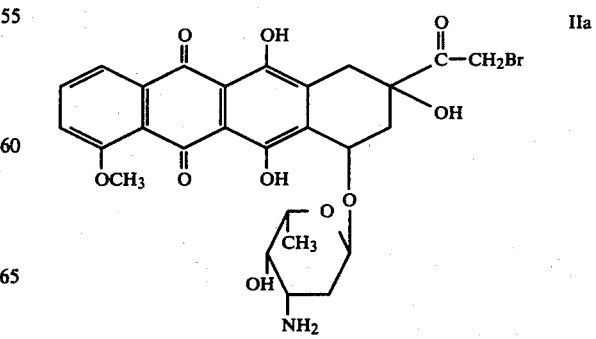

This simultaneous production of intermediates IIa and IIIa is believed to be at least partly responsible for the low yield of end-products I achieved by the prior art process.

The present inventors have carried out further research to develop an improved process for preparation of compounds I from daunomycin. During the course of this research, it was found that halogenation of daunomycin or an acid addition salt thereof using less methanol than in the prior art process decreases the yield of the ketal intermediate and allows the 14-halodaunomycin intermediate to be produced as the main product. Furthermore, the ketal intermediate which is now a by-product of halogenation may be easily converted into the 14-halodaunomycin intermediate II by treatment with acetone.

Conversion of the 14-halodaunomycin dimethylketal intermediate III to the 14-halodaunomycin intermediate II prior to etherification of the C-4' hydroxyl group enables the desired end-products of formula I to be obtained in higher yield and in greater purity than the prior art process and without the additional step of C-14 acylation to give ester intermediates VI.

The novel C-4' etherified 14-halodaunomycin intermediates IV produced according to the present process have been found to be easily hydrolyzed by alkaline hydrolysis to the desired end-products I. This is in contrast to the corresponding C-4' etherified 14-halodaunomycin dimethylketal intermediates which are much more resistant to hydrolysis.

To illustrate the overall process of the present invention, the following flow diagram is provided:

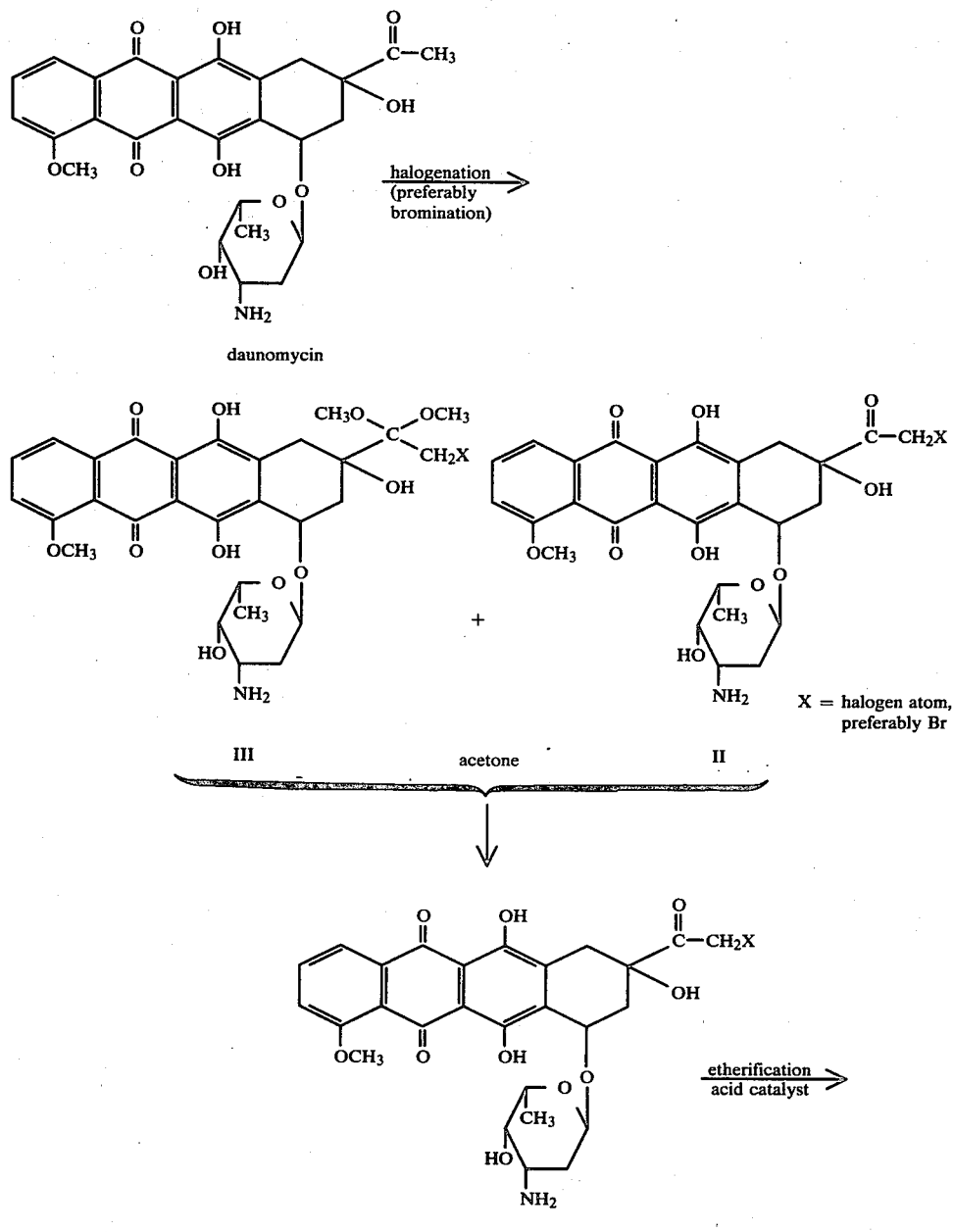

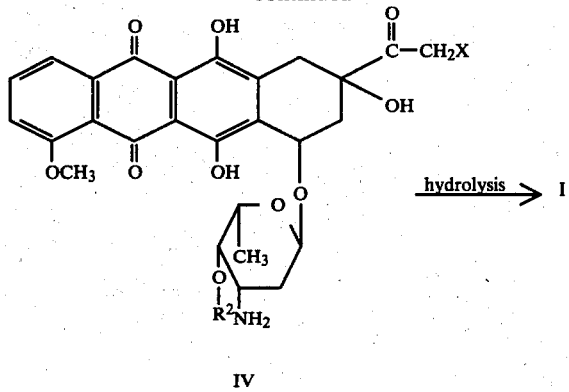

IV

In addition to the overall process described in the flow diagram, the present invention includes as preferred embodiments (1) the process of preparing compounds I from intermediates IV by alkaline hydrolysis; (2) the process of preparing compounds I from the 14-halodaunomycin intermediate II; and (3) the process of preparing novel intermediates IV from the 14-halodaunomycin intermediate II.

To elaborate on the present process, daunomycin or an acid addition salt such as the hydrochloride is halogenated (preferably iodinated or brominated and most preferably brominated) in an inert organic solvent in the presence of methanol. Halogenation of daunomycin is a known process, having been disclosed, for example, in U.S. Pat. Nos. 3,803,124 and 4,225,589 as well as in European patent application No. 14,853. Conventional halogenating agents (e.g. bromine, iodine) may be used in inert organic solvents such as methanol, methylene chloride and dioxane. By employing lower proportions of methanol than in the procedure of European patent application No. 14,853, it has been found that the halogenation can be directed to produce 14-halodaunomycin intermediate II as the major product with the co-produced ketal intermediate III being produced in reduced yields. As an example of a typical halogenation reaction, daunomycin hydrochloride dissolved in methanol may be brominated with a solution of bromine in methylene chloride in the presence of methyl orthoformate or dioxane and the resulting reaction mixture poured into dry diethyl ether to give a precipitated mixture of intermediates IIIa and IIa as described above.

The mixture of 14-halodaunomycin intermediate II and 14-halodaunomycin dimethylketal intermediate III, or acid addition salts thereof, obtained in the halogenation step is treated with acetone, preferably at room temperature, for a sufficient time (as monitored, e.g. by thin layer chromatography) to effect deketalisation of intermediate III to the desired keto intermediate II. Generally, about one hour at room temperature is sufficient for the deketalisation process.

Following the halogenation and deketalisation steps, the C-4' hydroxyl group of the 14-halodaunomycin intermediate II, or an acid addition salt thereof, is etherified as in the prior art process but without first esterifying intermediate II to form the prior art ester intermediates of formula V above. Etherification is carried out in the same manner as the etherification of intermediate V disclosed in European patent application No. 14,853, i.e. by reaction of dihydrofuran, dihydropyran, 2-acetoxymethyl-3,4-dihydro-2H-pyran, 2-methoxy-3,4-dihydro-2H-pyran, 2-carbomethoxy-3,4-dihydro-2H-pyran or an alkyl vinyl ether of the formula $CH_2=CHOR^1$ wherein $R^1$ is $C_1-C_8$ alkyl (preferably methyl, ethyl, n-butyl, isobutyl and 6-methylheptyl) or cyclohexyl in an inert organic solvent and in the presence of an acid catalyst.

Any nonreactive organic solvent may be used for the etherification step. Examples of suitable solvents include benzene, toluene, xylene, dimethylformamide, acetonitrile, tetrahydrofuran, dimethylsulfoxide and dioxane. The reaction solvent is preferably anhydrous and can be a single solvent or mixture of solvents. A most preferred solvent is anhydrous dimethylformamide.

The acid catalyst used in the etherification step may be any organic (e.g. formic, trifluoroacetic) or inorganic (e.g. hydrochloric, phosphoric) acid. A preferred class of acid catalysts comprises the organic sulfonic acids. More preferred catalysts are the aromatic sulfonic acids such as p-toluenesulfonic acid, benzenesulfonic acid or DL-camphorsulfonic acid. Especially advantageous combinations of solvents and acid catalysts are p-toluenesulfonate in anhydrous dimethylformamide, p-toluenesulfonate in a mixture of anhydrous dimethylsulfoxide and anhydrous tetrahydrofuran and DL-camphorsulfonate in anhydrous dimethylformamide.

The etherification reaction temperature is not critical. Good results have been achieved at room temperature, although temperatures higher or lower than this may also be used. Generally, the etherification can be completed in from about 20 minutes to 50 hours at room temperature.

Hydrolysis of the C-4' etherified intermediates of formula IV, or acid addition salts thereof, may be accomplished by basic hydrolysis. Thus, intermediate IV may be reacted with a water-miscible organic solvent such as a $C_1-C_6$ alkanol (e.g. methanol or ethanol) or aqueous acetone at room temperature or with mild heating in the presence of base, e.g. aqueous sodium hydroxide. The progress of the dehalogenation reaction may be monitored by thin layer chromatography.

The products obtained upon hydrolysis may be in the form of the free base, an acid addition salt thereof or a nontoxic acid addition salt thereof. Free base products may be easily converted into nontoxic acid addition salts by known methods (see, for example, U.K. patent application No. 2,002,754A and European patent application No. 14,853). Thus, the free base may be reacted with a nontoxic acid in a suitable solvent and the salt recovered by lyophilization or by precipitation with an antisolvent. Products in the form of an acid addition salt may be converted to the corresponding free base by neutralization with a basic substance. Finally, toxic acid addition salts may be converted to nontoxic acid addition salts by neutralization and treatment with a nontoxic acid as described above.

The C-4' etherified products obtained by the etherification procedure of the present invention are a diastereomeric mixture of isomers arbitrarily designated as a and b. The individual diastereomers may be separated and purified by conventional methods. For example, the mixture of diastereomers may be separated by column or thin layer chromatography (using alumina, silica gel, etc.). Diastereomers a and b seem to have absolute configuration R and S at the chiral center since the two isomers differ in the chemical shift of the methine protons corresponding to the chiral center.

The following examples are provided for illustrative purposes only and are not intended to limit the scope of the invention. The term "ether" as used in the examples below refers to diethyl ether.

EXAMPLE 1

4'-O-Tetrahydropyranyladriamycins a and b

14-Bromodaunomycin hydrochloride (6.0 g) is dissolved in 100 ml of anhydrous dimethylformamide. To this solution, 25 ml of dihydropyran and 25 mg of DL-camphorsulfonic acid are added and allowed to react at 25° C. for 6 hours. Monitoring by silica gel thin layer chromatography (chloroform:methanol=9:1 by volume) reveals the formation of two new compounds having Rf values of 0.32 and 0.44 with the concomitant disappearance of the starting material. The reaction mixture is poured into a mixture of 1 liter acetone and 500 ml water and is kept at pH 11±0.1 under vigorous agitation with 0.5 N trisodium phosphate. The two compounds having the said Rf values are found to change slowly to new products having Rf values of 0.12 and 0.23 by thin layer chromatography. After reaction for one hour at 25° C., the solution is neutralized by 1 N hydrochloric acid and acetone is removed by evaporation under reduced pressure. The concentrate is extracted twice with 500 ml and 200 ml of methylene chloride. The methylene chloride extracts are combined, rinsed three times with 500 ml of water and then dried over anhydrous sodium sulfate. The methylene chloride solution is charged on a column of 50 g silica gel (E. Merck, Darmstadt; Kieselgel 60, 70–230 mesh) and the column is washed with 1 liter of chloroform. Chloroform-methanol mixture is used for elution. Each 20 ml fraction is monitored by thin layer chromatography for product analysis. Fractions containing a product of Rf 0.23 are combined and concentrated under reduced pressure to provide 1.7 g of dark red solids of 4'-O-tetrahydropyranyladriamycin b (yield 29%). Recrystallization from methylene chloride gives 0.54 g of the above product in the pure state. Melting point under decomposition: 191°–192° C.

NMR(CDCl$_3$, ppm) 1.33(6'-H), 1.50~1.96(tetrahydropyranyl-H), 4.07(4'-O-methyl-H), 4.73(14-H), 4.72(anomeric H of the tetrahydropyranyl group), 5.27(1'-H), 7.31~8.06 (1~3-H).

IR(KBr, cm$^{-1}$) 3680, 3530, 3390, 1720, 1618, 1578, 1407, 1294, 1209, 1121, 1110, 1075, 1000, 988, 960, 815, 761.

$[\alpha]_D^{19}$ +202.7° (c=0.75, CHCl$_3$)

Fractions containing the product with Rf 0.13 give 0.65 g of 4'-O-tetrahydropyranyladriamycin a.

EXAMPLE 2

Daunomycin hydrochloride (226 mg) is dissolved in 4 ml of anhydrous methanol and is mixed with 0.2 ml of methyl orthoformate and 8 ml of dioxane. After 0.83 ml of bromine solution in methylene chloride (10% w/v) is added, the reaction is carried out at 25° C. for 40 minutes. The reaction mixture is poured into 50 ml of dry diethylether and the precipitates formed are recovered by centrifugation. The supernatant solution is discarded. After washing twice with 5 ml of dry ether, the precipitates are treated under agitation in 12 ml of acetone at 25° C. for one hour. The treated deposits are collected by centrifugation, rinsed twice with ether and dried to give 226 mg of red powder of 14-bromodaunomycin hydrochloride (yield 87%). The red powder is dissolved in 7 ml of dry dimethylformamide and mixed with 2 ml of dihydropyran and 10 mg of p-toluenesulfonic anhydride. After reaction at 20° C. for 3 hours, the reaction mixtue is poured into a mixture of 60 ml acetone and 30 ml water and allowed to stand for 30 minutes at pH 11.0–11.5 under control with 1 N sodium hydroxide. The solution is neutralized with diluted hydrochloric acid and most of the acetone is evaporated off under reduced pressure. The concentrate is extracted three times with 30 ml of chloroform. The chloroform extracts are combined, rinsed three times with water and dried over anhydrous sodium sulfate. The chloroform solution is concentrated under reduced pressure to give dark red solids. Purification is performed with silica gel thin layer plates (E. Merck, Darmstadt; silica gel 60, 20×20 cm, 2 mm thick). Satisfactory separation is obtained by developing with a solvent mixture of chloroform and methanol (9:1 v/v). Silica gel powder corresponding to the area of Rf 0.23 is scraped off and eluted with a mixture of chloroform and methanol (2:1 v/v). The eluate is concentrated to dryness under reduced pressure to provide 54 mg of reddish brown solid of 4'-O-tetrahydropyranyladriamycin b (overall yield 21%).

Similarly 39 mg of 4'-O-tetrahydropyranyladriamycin a (overall yield 16%) is recovered from the area of Rf 0.13.

EXAMPLE 3

4'-O-Tetrahydrofuranyladriamycin

14-Bromodaunomycin hydrochloride (1.10 g) in 30 ml of dry dimethylformamide is mixed with 0.2 ml of dihydrofuran and a small amount of DL-camphorsulfonic acid and then allowed to react at a temperature of 20°–25° C. for 3 hours. The reaction solution is diluted with a mixture of 200 ml acetone and 100 ml water and stirred vigorously for one hour while the pH of the solution is maintained at 11±0.1 by addition of 0.5 N trisodium phosphate. After neutralization with 1 N hydrochloric acid, the acetone is removed by evaporation in vacuo. The concentrate is submitted to extraction twice with 50 ml of methylene chloride and the methylene chloride extracts are combined and rinsed three times with water. The methylene chloride solution is passed through a column of 20 g silica gel (E. Merck, Darmstadt; Silica gel 60) and the adsorbed products are eluted with a solvent system of chloroform and methanol under monitoring by thin layer chromatography (chloroform:methanol=9:1 by volume). Fractions containing compounds of Rf 0.16 and 0.19 are collected and concentrated to dryness to give 350 mg of dark red solid of 4'-O-tetrahydrofuranyladriamycin (yield 33%).

Melting point under decomposition: 189°–194° C.
NMR(CDCl$_3$, ppm) 1.25~1.27(6'methyl-H), 1.67~2.30 (tetrahydrofuranyl-H), 4.07(4-O-methyl-H), 4.75(14-H), 5.17 and 5.38(anomeric H of the tetrahydrofuranyl group), 5.30(1'-H), 7.30~8.07(1~3-H).

EXAMPLE 4

Adriamycin Hydrochloride

To a solution of 226 mg of daunomycin hydrochloride in 4 ml of anhydrous methanol, 0.2 ml of methyl orthoformate and 8 ml of dioxane are added. After 0.83 ml of bromine-methylene chloride solution (10%, w/v) is added, the reaction is carried out at 25° C. for 40 minutes. The reaction solution is diluted with 50 ml of dry ether and the formed precipitates are collected by centrifugation, whereas the supernatant is discarded. The precipitates are washed twice with 5 ml of dry ether and then treated under agitation with 12 ml of acetone at 25° C. for one hour. After dilution with aqueous acetone, the acetone solution is kept for 20 minutes at pH 11±0.1 by adjusting with 0.5 M sodium phosphate. The treated solution is neutralized and the acetone is evaporated off in vacuo. The product is extracted repeatedly with a chloroform-methanol mixture and the extracts are combined and dried over anhydrous sodium sulfate.

After concentration in vacuo, adriamycin hydrochloride is forced to precipitate by adding methanolic hydrochloride acid and anhydrous ether to the chloroform concentrate.

Melting point under decomposition: 204°~205° C.
$[\alpha]_D^{20}$ +248°(c=0.1, CH$_3$OH).

By following the general procedures of Examples 1–4, several other C-4' etherified products were prepared. Table 1 below shows that various end-products produced according to the process of the present invention and the overall yield based on daunomycin.

TABLE 1

Yields of C-4'Etherified Products Produced by Present Process

| Product** | Example No. | R$^2$Substituent* | Yield*** |
|---|---|---|---|
| 4'-O—(tetrahydropyranyl) ADM (a) | 2 |  | 16% |
| 4'-—(tetrahydropyranyl) ADM (b) | 2 |  | 21% |
| 4'-O—(tetrahydrofuranyl)- ADM | 3 |  | 46% |
| 4'-O—(6-acetoxymethyltetrahydropyranyl) ADM | 4 |  | 37% |
| 4'-O—(1-ethoxyethyl)- ADM (a) | 5 |  | 25% |
| 4'-O—(1-ethoxyethyl)- ADM (b) | 5 |  | 24% |
| 4'-O—(1-butyloxyethyl)- ADM (a) | 6 |  | 14% |
| 4'-O—(1-butyloxyethyl)- ADM (b) | 6 |  | 17% |
| 4'-O—(1-isobutyloxyethyl)- ADM (a) | 7 |  | 18% |
| 4'-O—(1-isobutyloxyethyl)- ADM (b) | 7 |  | 19% |
| 4'-O—(1-(6-methylheptyloxy)-ethyl- ADM (a) | 8 |  | 15% |
| 4'-O—(1-(6-methylheptyloxy)-ethyl- ADM (b) | 8 |  | 18% |
| 4'-O—(1-cyclohexyloxyethyl)- ADM (a) | 9 |  | 16% |

TABLE 1-continued

Yields of C-4'Etherified Products Produced by Present Process

| Product** | Example No. | R²Substituent* | Yield*** |
|---|---|---|---|
| 4'-O—(1-cyclohexyloxyethyl)- ADM (b) | 9 | 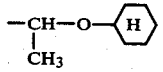 | 17% |

*in formula I
**ADM = adriamycin
***overall based on daunomycin starting material

We claim:

1. A compound having the formula

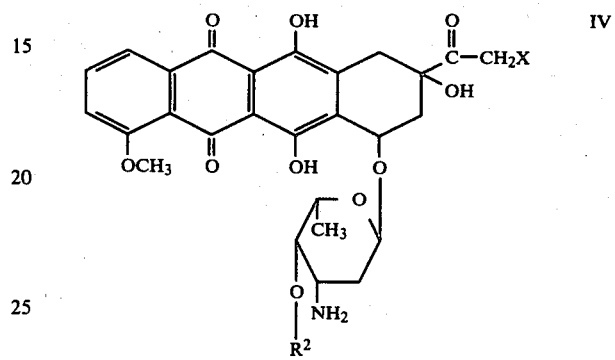

wherein X is bromine or iodine and $R^2$ is tetrahydropyranyl, 6-acetoxymethyltetrahydropyranyl, 6-methoxytetrahydropyranyl, 6-carbomethoxytetrahydropyranyl, tetrahydrofuranyl, $C_1$-$C_8$ alkyloxyethyl or cyclohexyloxyethyl, or an acid addition salt thereof.

2. A compound of claim 1 wherein X is bromine or iodine and $R^2$ is tetrahydropyranyl, 6-acetoxymethyltetrahydropyranyl, 6-methoxytetrahydropyranyl, 6-carbomethoxytetrahydropyranyl, tetrahydrofuranyl, 1-methoxyethyl, 1-ethoxyethyl, 1-butyloxyethyl, 1-isobutyloxyethyl, 1-(6-methylheptyloxy)ethyl or cyclohexyloxyethyl, or an acid addition salt thereof.

3. A compound of claim 1 or claim 2 wherein X is bromine, or an acid addition salt thereof.

* * * * *